US010827755B2

(12) United States Patent
Crawford et al.

(10) Patent No.: US 10,827,755 B2
(45) Date of Patent: Nov. 10, 2020

(54) INSECTICIDAL COMPOSITIONS AND METHODS

(71) Applicant: Monsanto Technology LLC, St. Louis, MO (US)

(72) Inventors: Michael J. Crawford, St. Louis, MO (US); Matthew Dimmic, St. Louis, MO (US); Rae Lawrence, St. Louis, MO (US); Christina Marie Taylor, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 81 days.

(21) Appl. No.: 15/777,124

(22) PCT Filed: Nov. 9, 2016

(86) PCT No.: PCT/US2016/061033
§ 371 (c)(1),
(2) Date: May 17, 2018

(87) PCT Pub. No.: WO2017/087218
PCT Pub. Date: May 26, 2017

(65) Prior Publication Data
US 2018/0325112 A1 Nov. 15, 2018

Related U.S. Application Data

(60) Provisional application No. 62/256,867, filed on Nov. 18, 2015.

(51) Int. Cl.
| | | |
|---|---|---|
| *A01N 43/50* | (2006.01) |
| *A01N 43/56* | (2006.01) |
| *C07D 405/12* | (2006.01) |
| *C07D 409/04* | (2006.01) |
| *C07D 409/12* | (2006.01) |
| *C07D 233/58* | (2006.01) |
| *A01N 25/00* | (2006.01) |
| *C07D 233/64* | (2006.01) |
| *C07D 233/90* | (2006.01) |

(52) U.S. Cl.
CPC .............. *A01N 43/50* (2013.01); *A01N 25/00* (2013.01); *A01N 43/56* (2013.01); *C07D 233/58* (2013.01); *C07D 233/64* (2013.01); *C07D 233/90* (2013.01); *C07D 405/12* (2013.01); *C07D 409/04* (2013.01); *C07D 409/12* (2013.01)

(58) Field of Classification Search
CPC ........ A01N 43/56; A01N 25/00; A01N 43/50; C07D 233/90; C07D 233/64; C07D 409/04; C07D 233/58; C07D 409/12; C07D 405/12
USPC ...................................................... 514/396
See application file for complete search history.

(56) References Cited

U.S. PATENT DOCUMENTS

| | | | |
|---|---|---|---|
| 3,212,966 A | 10/1965 | Krause | |
| 3,707,475 A | 12/1972 | Lombardino | |
| 3,784,557 A | 1/1974 | Cescon | |
| 5,163,990 A | 11/1992 | Rebeiz | |
| 2004/0142984 A1 | 7/2004 | Lahm et al. | |
| 2004/0259913 A1 | 12/2004 | Clark | |
| 2006/0052343 A1 | 3/2006 | Lahm et al. | |
| 2006/0167060 A1 | 7/2006 | Lahm et al. | |
| 2009/0269300 A1 | 10/2009 | Finkelstein et al. | |
| 2010/0099692 A1 | 4/2010 | Natsuhara et al. | |
| 2011/0312953 A1* | 12/2011 | Fischer .................. | A01N 43/56 514/230.5 |
| 2014/0249025 A1 | 9/2014 | Pahutski, Jr. et al. | |
| 2015/0158820 A1 | 6/2015 | Fujita | |

FOREIGN PATENT DOCUMENTS

| | | | |
|---|---|---|---|
| CN | 102464592 B | | 9/2014 |
| CN | 104945326 B | * | 3/2017 |
| JP | H03-232861 A | | 10/1991 |
| JP | H09-176614 A | | 7/1997 |
| WO | 2007/083207 A1 | | 7/2007 |

OTHER PUBLICATIONS

English Translation of CN '326 CN104945326B, claiming priority to Jun. 24 2015. (Year: 2015).*
International Search Report issued in Application No. PCT/US2016/061033 dated Mar. 24, 2017.
Chemical Abstracts Database Accession No. 1971:497974, Document No. XP-002789245, Cohen, R. L., Substituent Effects on the Reactivity of Triarylimidazolyl Free Radicals Toward Tris(2-methyl-4-diethylaminophenyl) Methane, Journal of Organic Chemistry, 1971, pp. 2280-2284, vol. 36, No. 16.
Chemical Abstracts Database Accession No. 1971:497973, Document No. XP-002789246, Coraor, G. R., et al., "Properties of Triarylimidazolyl Radicals and Their Dimers," Journal of Organic Chemistry, 1971, pp. 2262-2267, vol. 36, No. 16.
Chemical Abstracts Database Accession No. 1999:430541, Document No. XP-002789247, Isikdag, I., et al., Syntheses and Analgesic Activities of Some 2-substituted-4,5-diphenyl and 1,2-disubstituted-4,5-diphenyl Imidazole Derivatives, Bollettino Chimico Farmaceutico, 1999, pp. 24-29, vol. 138, No. 1.

(Continued)

*Primary Examiner* — Kortney L. Klinkel
*Assistant Examiner* — William Y Lee
(74) *Attorney, Agent, or Firm* — Stinson LLP; Lawrence M. Lavin, Jr.

(57) ABSTRACT

Substituted imidazole and substituted pyrazole compounds and compositions derived therefrom can be useful in controlling insect pests. Suitable imidazole compounds can be analogues of 2,4,5-triphenyl-1H-imidazole, wherein the C-2 phenyl group bears at least one substitution, the C-4 and C-5 phenyl groups are optionally substituted, and N-1 is unsubstituted. Suitable pyrazole compounds can bear a 1,3,4-substitution pattern, with an optionally substituted aryl or optionally substituted alkyl group being present at N-1, an optionally substituted aryl or optionally substituted heteroaryl group being present at C-3, and a secondary amide group being present at C-4. These compounds and compositions derived therefrom can be administered to a plant, seed, soil or insect to control a variety of insect pests.

16 Claims, No Drawings

(56) References Cited

OTHER PUBLICATIONS

Chemical Abstracts Database Accession No. 2015:1839421, Document No. XP-002789244, Mahdavi, M., et al., "Synthesis of New Benzo[f]imidazo[1,2-d] [1,4]oxazepines: AgNO3-mediated Intramolecular Hydroamination," Tetrahedron Letters, 2015, pp. 7082-7084, vol. 56, No. 51.
Partial Supplementary European Search Report issued for EP16866863.0 dated May 9, 2019, 22 pages.
Chemical Abstracts Database Accession No. 2016:1665569, Document No. XP-002792940, Li, L., et al., Design, Synthesis and Biological Activity of Novel Substituted Diamides Derivatives Containing Thiophene Ring, 2016, Gaodeng Xuexiao Huaxue Suebao, 35/9:1649-1654. 1 Page.
Coraor, L.A., et al., "Properties of Triarylimidazolyl Radicals and Their Dimers," 1971, J Org Chem, 36/16:2262-2267. First Page Only.

\* cited by examiner

INSECTICIDAL COMPOSITIONS AND METHODS

CROSS-REFERENCE TO RELATED APPLICATIONS

The present application claims the benefit of priority under 35 U.S.C. § 119 from U.S. Provisional Patent Application 62/256,867, filed on Nov. 18, 2015 and incorporated herein by reference in its entirety.

STATEMENT REGARDING FEDERALLY SPONSORED RESEARCH OR DEVELOPMENT

Not applicable.

FIELD

The present application generally relates to insect control and, more specifically, to compositions and methods employing substituted imidazole and substituted pyrazole compounds for use in controlling insect pests.

BACKGROUND

Insect pests can cause significant losses in agriculture, which can impact food production yields and result in increased costs to the consumer. Effective control of invertebrate pests can contribute to more efficient crop production.

Among the insect pests that are particularly undesirable are those that can significantly impact the yield of important row crops including, for example, corn, soybeans, cotton and certain other types of vegetables. Examples of insect pests that can have a destructive impact on these crops include, but are not limited to, fall armyworm, Western corn rootworm, diamondback moth, Western tarnished plantbug and soybean looper.

Ornamental plants or other types of plants not being cultivated as a food source can be similarly impacted by a range of insect pests. Different insect pests may impact these types of plants.

Insect pests can also represent a nuisance or health hazard to both humans and animals. Because of their proximity to insect-targeted agricultural products, agricultural workers can oftentimes be particularly affected. Mosquitoes are one of many examples of insect pests that can be a nuisance or health hazard to humans and animals.

Although products for controlling insect pests are commercially available, the need continues for new formulations that are more effective, less costly, environmentally safer, and/or exhibit new modes of action. Identifying new compounds that have improved activity against insect pests can be a driving factor in the search for formulations having improved insecticidal activity.

SUMMARY

Compounds that exhibit insecticidal activity are described herein. The compounds described herein may be used, for example, in the preparation of compositions and in accordance with methods for control of insect pests, as set forth in detail below. More particularly, compositions and methods employing substituted imidazole and substituted pyrazole compounds for use in controlling insect pests are described herein.

In some embodiments, methods of the present disclosure comprise administering to a plant, seed, soil or insect, a composition comprising a compound of Formula I, a tautomer thereof or a salt thereof

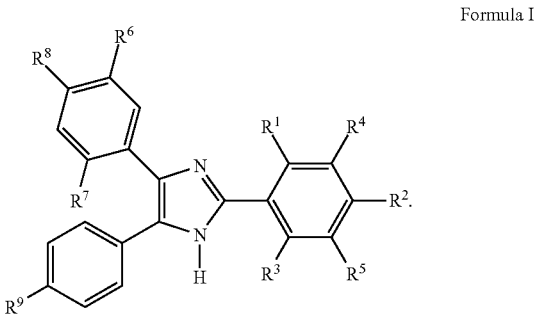

Formula I $R^1$, $R^2$ and $R^3$ are independently selected from the group consisting of hydrogen, halogen, alkyl, alkoxy, thioalkyl, alkenyloxy, alkynyloxy, haloalkyl and haloalkoxy. $R^4$ and $R^5$ are independently selected from the group consisting of hydrogen, halogen, alkyl, alkoxy, alkenoxy and alkynoxy. At least one of $R^1$-$R^5$ is not hydrogen. $R^6$ and $R^7$ are independently selected from the group consisting of hydrogen, halogen and alkyl. $R^8$ is selected from the group consisting of hydrogen, alkyl and optionally substituted acylphenyl.

Treatment compositions comprising the compound of Formula I, a tautometer thereof or a salt thereof are also described.

Treated seeds can be prepared by administering the compound of Formula I, a tautomer thereof or a salt thereof to a seed, in which the treated seed comprises the compound of Formula I.

In some or other illustrative embodiments, methods of the present disclosure comprise administering to a plant, seed, soil or insect, a composition comprising a compound of Formula II or a salt thereof

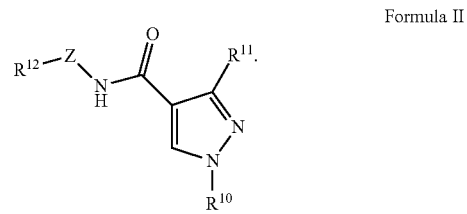

Formula II $R^{10}$ is selected from the group consisting of optionally substituted aryl and optionally substituted alkyl. $R^{11}$ is selected from the group consisting of optionally substituted aryl and optionally substituted heteroaryl. $R^{12}$ is selected from the group consisting of optionally substituted alkyl, optionally substituted alkenyl, optionally substituted alkynyl, optionally substituted alkoxy, optionally substituted heterocycloalkyl and optionally substituted, fully saturated cycloalkyl. Z is $C_1$-$C_6$ alkyl or a bond.

Treatment compositions comprising the compound of Formula II or a salt thereof are also described.

Treated seeds can be prepared by administering the compound of Formula II or a salt thereof to a seed, in which the treated seed comprises the compound of Formula II.

DETAILED DESCRIPTION

Compounds that exhibit insecticidal activity are described herein. The compounds described herein may be used, for example, in the preparation of compositions and in accordance with methods for control of insect pests, as set forth in detail below. More particularly, compositions and methods employing substituted imidazole and substituted pyrazole compounds for use in controlling insect pests are described herein.

As used herein, the term "insect pest" refers to any insect that infests a plant or a planting site, or that is a nuisance insect toward a human or an animal. More specific examples of insect pests are provided hereinbelow.

The present disclosure provides a number of compounds that have beneficial activity toward controlling insect pests. Substituted imidazole and substituted pyrazole compounds of the types discussed herein can be used for this purpose. These compounds can be used alone or in combination with one another for controlling insect pests. Depending upon the substituents present in the compounds, some insect pests can be targeted in preference to others.

In some embodiments, compounds suitable for controlling insect pests can be a compound of Formula I, a tautomer thereof, or a salt thereof

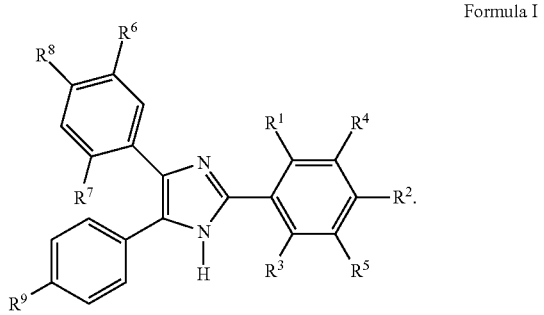

Formula I $R^1$, $R^2$ and $R^3$ are independently selected from the group consisting of hydrogen, halogen, alkyl, alkoxy, thioalkyl, alkenyloxy, alkynyloxy, haloalkyl and haloalkoxy. $R^4$ and $R^5$ are independently selected from the group consisting of hydrogen, halogen, alkyl, alkoxy, alkenoxy and alkynoxy. At least one of $R^1$-$R^5$ is not hydrogen. $R^6$ and $R^7$ are independently selected from the group consisting of hydrogen, halogen and alkyl. $R^8$ is selected from the group consisting of hydrogen, alkyl and optionally substituted acylphenyl. $R^9$ is selected from the group consisting of hydrogen and alkyl.

In some or other embodiments, compounds suitable for controlling insect pests can be a compound of Formula II or a salt thereof.

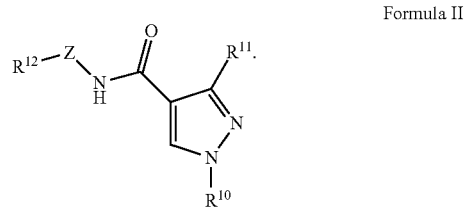

Formula II $R^{10}$ is selected from the group consisting of optionally substituted aryl and optionally substituted alkyl. $R^{11}$ is selected from the group consisting of optionally substituted aryl and optionally substituted heteroaryl. $R^{12}$ is selected from the group consisting of optionally substituted alkyl, optionally substituted alkenyl, optionally substituted alkynyl, optionally substituted alkoxy, optionally substituted heterocycloalkyl and optionally substituted, fully saturated cycloalkyl. Z is $C_1$-$C_6$ alkyl or a bond.

As used herein, the term "tautomer" refers to any compound existing in at least two forms that readily interconvert, with a state of equilibrium being established between the at least two forms.

As used herein, the term "halogen" refers to any radical of fluorine, chlorine, bromine or iodine.

As used herein, the term "alkyl" refers to, by itself or as part of another group, both straight and branched chain radicals of up to ten carbons, which may be optionally independently substituted. Non-limiting examples of $C_1$-$C_{10}$ alkyl groups include methyl, ethyl, propyl, isopropyl, butyl, sec-butyl, t-butyl, pentyl, isopentyl, hexyl, heptyl, and octyl groups. In some embodiments of the present disclosure, the term "alkyl" refers to, by itself or as part of another group, a straight or branched chain radical comprising from one to six carbon atoms, or from one to three carbon atoms.

As used herein, the term "haloalkyl" refers to, by itself or as part of another group, an alkyl group substituted with at least one halogen. Non-limiting examples of haloalkyl groups include trifluoromethyl and 2,2,2-trifluoroethyl.

As used herein, the term "alkoxy" refers to, by itself or as part of another group, an alkyl group appended to a parent molecular entity through an oxygen atom. Non-limiting examples of alkoxy groups include methoxy, ethoxy, propoxy, 2-propoxy, 1-butoxy, 2-butoxy, tert-butoxy, l-pentoxy, 2-pentoxy, 3-pentoxy, 1-hexoxy, 2-hexoxy, and 3-hexoxy.

As used herein, the term "thioalkyl" refers to the sulfur analogue of an alkoxy group, in which, by itself or as part of another group, an alkyl group is appended to a parent molecular entity through a sulfur atom.

As used herein, the term "haloalkoxy" refers to, by itself or as part of another group, an alkoxy group in which the appended alkyl group is further substituted with at least one halogen. Non-limiting examples of haloalkoxy groups include trifluoromethoxy, 2,2-dichloroethoxy, and 2,2,2-trifluoroethoxy.

As used herein, the term "cycloalkyl" refers to an alkyl group forming a closed ring comprising from 3 to 8 carbon atoms or from 6 to 10 carbon atoms, which may be optionally substituted. Non-limiting examples of cycloalkyl groups include cyclopropyl, cyclobutyl, cyclopentyl, cyclohexyl, methylcyclohexyl, and cycloheptyl. The term "cycloalkyl" further refers to any of monocyclic, bicyclic and polycyclic carbon-containing rings.

As used herein, the term "optionally substituted" refers to a moiety that may be present as a pendant group attached to a carbon-containing ring or chain. In some embodiments, an optional substitution may be a pendant group comprising at least one heteroatom. As used herein, the term "heteroatom" refers to oxygen, nitrogen, sulfur or halogen atoms.

As used herein, the term "heterocycloalkyl" refers to a saturated or partially saturated monocyclic or bicyclic hydrocarbon containing one or more heteroatoms selected from O, S, and N, which replace one or more carbon atoms within the carbon-containing ring. A heterocycloalkyl group may be attached to a parent molecular entity via any of the carbon atoms or, if present, a nitrogen atom. Non-limiting examples of heterocycloalkyl groups include, but are not limited to, 4-membered rings, such as an azetidinyl, and oxetanyl; 5-membered rings, such as tetrahydrofuranyl, dioxolinyl, pyrrolidinyl, pyrrolidinonyl, imidazolidinyl, pyrazolidinyl, and pyrrolinyl; 6-membered rings, such as tetrahydropyranyl, tetrahydrothiopyranyl, piperidinyl, morpholinyl, dithianyl, thiomorpholinyl, piperazinyl, and trithianyl; or 7-membered rings, such as a diazepanyl ring, for example.

As used herein, the term "aryl" refers to, by itself or as part of another group, a monocyclic, bicyclic or tricyclic aromatic group containing from 6 to 14 carbon atoms. Common aryl groups include $C_6$-$C_{14}$ aryl, particularly $C_6$-$C_{10}$ aryl. Non-limiting examples of $C_6$-$C_{14}$ aryl groups include phenyl, naphthyl, phenanthrenyl, anthracenyl, indenyl, azulenyl, biphenyl, biphenylenyl and fluorenyl groups.

As used herein, the term "heteroaryl" refers to, by itself or as part of another group, a cyclic moiety having 5 to 14 ring atoms and 6, 10 or 14 π electrons shared in a cyclic array, in which 1, 2 or 3 of the ring atoms are oxygen, nitrogen, and/or sulfur atoms and the remaining ring atoms are carbon atoms. Non-limiting examples of heteroaryl groups include thienyl (thiophenyl), benzo[b]thienyl, naphtho[2,3-b]thienyl, thianthrenyl, furyl (furanyl), pyranyl, isobenzofuranyl, chromenyl, xanthenyl, phenoxanthinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, carbazolyl, β-carbolinyl, phenanthridinyl, acrindinyl, pyrimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-α]pyrimidin-4-one, pyrazolo[1,5-α]pyrimidinyl, including without limitation pyrazolo[1,5-α]pyrimidin-3-yl, 1,2-benzoisoxazol-3-yl, benzimidazolyl, 2-oxindolyl and 2-oxobenzimidazolyl. In instances where a heteroaryl group contains a nitrogen atom in a ring, the nitrogen atom may optionally be in the form of an N-oxide, such as pyridyl N-oxide, pyrazinyl N-oxide or pyrimidinyl N-oxide, for example.

As used herein, the term "alkenyl" refers to a straight- or branched-chain alkyl group in which at least one carbon-carbon double bond has replaced a carbon-carbon single bond. The at least one carbon-carbon double bond can be in any location and in either the E or Z configuration. Non-limiting examples of alkenyl radicals include ethenyl, E- and Z-propenyl, 2-propenyl (allyl), E- and Z-butenyl, E- and Z-isobutenyl, E- and Z-pentenyl, E- and Z-hexenyl, E,E-, E,Z-, Z,E-, Z,Z-hexadienyl, and the like.

As used herein, the term "alkynyl" refers to a straight- or branched-chain alkyl group in which at least one carbon-carbon triple bond has replaced a carbon-carbon single bond. Non-limiting examples of alkynyl groups include $CH_2$—C≡CH (propargyl), $CH_2$—C≡C—$CH_3$, and $CH_2$—C≡C—CH($CH_3$)—$CH_2$—$CH_3$ As used herein, the terms "alkenyloxy" and "alkynyloxy" refer to an alkenyl group or an alkynyl group, respectively, which are appended to a parent molecular entity through an oxygen atom.

As used herein, the term "acylphenyl" refers to a phenyl group appended to a parent molecular entity through a carbonyl moiety.

As one having ordinary skill in the art will understand, N-unsubstituted imidazole compounds are tautomeric and interconvert between the 1H and 3H forms. The equilibrium distribution between the 1H and the 3H forms can depend upon a number of factors including, for example, pH, temperature and the type of substituents that are present on the imidazole group. Accordingly, it is to be understood that any reference herein to a compound having the structure of Formula I also equivalently refers to the tautomeric 3H structure of Formula I', or an equilibrium mixture of compounds having the structures of Formulas I and I'.

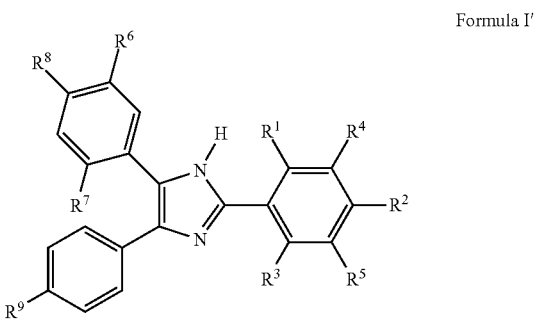

Formula I'

Compounds having the structure of Formula II are believed to be substantially non-tautomeric.

In some embodiments, the compositions comprise a compound, tautomer or salt of Formula I, in which $R^1$, $R^2$ and $R^3$ are independently selected from the group consisting of hydrogen, halogen, alkyl, alkoxy, thioalkyl, and alkynyloxy. In some or other embodiments, the compositions comprise a compound, tautomer or salt of Formula I, in which $R^1$, $R^2$ and $R^3$ are independently selected from the group consisting of hydrogen, halogen, alkyl, alkoxy, and alkynyloxy.

In some embodiments, the compositions comprise a compound, tautomer or salt of Formula I, in which $R^1$, $R^2$ and $R^3$ are each alkyl, and in more particular embodiments, $R^1$, $R^2$ and $R^3$ are each methyl. In still more particular embodiments, $R^1$, $R^2$ and $R^3$ are each methyl and $R^4$-$R^9$ are each hydrogen.

In some embodiments, the compositions comprise a compound, tautomer or salt of Formula I, in which $R^1$ and $R^2$ are each alkyl, and in more particular embodiments, $R^1$ and $R^2$ are each methyl.

In some embodiments, the compositions comprise a compound, tautomer or salt of Formula I, in which $R^1$ and $R^3$ are each halogen, or $R^1$ and $R^2$ are each halogen. In more particular embodiments, $R^1$ and $R^3$ are each chlorine, or $R^1$ is chlorine and $R^3$ is fluorine, or $R^1$ and $R^2$ are each chlorine. In still more particular embodiments, $R^1$ and $R^3$ are each chlorine, $R^6$ and $R^7$ are each methyl, and $R^2$, $R^4$, $R^5$, $R^8$ and $R^9$ are each hydrogen; or $R^1$ is chlorine, $R^3$ is fluorine, $R^6$ and $R^7$ are each methyl, and $R^2$, $R^4$, $R^5$, $R^8$ and $R^9$ are each hydrogen; or $R^1$ and $R^2$ are each chlorine, $R^6$ is chlorine, and $R^3$, $R^4$, $R^5$, $R^7$, $R^8$ and $R^9$ are each hydrogen.

In some embodiments, the compositions comprise a compound, tautomer or salt of Formula I, in which one or both of $R^4$ and $R^5$ is/are halogen, and in more particular embodiments, $R^4$ and/or $R^5$ is chlorine or fluorine. In still more particular embodiments, $R^4$ is fluorine, $R^9$ is acylphenyl or acyl(4-fluorophenyl), and $R^1$-$R^3$ and $R^1$-$R^8$ are hydrogen.

In some embodiments, the compositions comprise a compound, tautomer or salt of Formula I, in which at least one of $R^1$ and $R^2$ is alkoxy, and in more particular embodiments $R^1$ and $R^2$ are each methoxy, or $R^1$ is ethoxy, or $R^2$ is methoxy. In still more particular embodiments, $R^1$ and $R^2$ are each methoxy, and $R^3$-$R^9$ are hydrogen; or $R^1$ is ethoxy and $R^2$-$R^9$ are hydrogen; or $R^2$ is methoxy, $R^4$ and $R^5$ are each methoxy, and $R^1$, $R^3$ and $R^6$-$R^9$ are hydrogen.

In some embodiments, the compositions comprise a compound, tautomer or salt of Formula I, in which $R^1$ is alkynyloxy, and in more specific embodiments, $R^1$ is propargyloxy. In still more particular embodiments, $R^1$ is propargyloxy and $R^2$-$R^9$ are hydrogen.

In some embodiments, the compositions comprise a compound, tautomer or salt of Formula I, in which $R^2$ is thioalkyl, and in more specific embodiments, $R^2$ is thiomethyl. In still more specific embodiments, $R^2$ is thiomethyl, $R^1$ is methyl, and $R^1$, $R^3$-$R^7$, and $R^9$ are hydrogen.

In some embodiments, the compositions comprise a compound, tautomer or salt of Formula I, in which $R^1$ is hydrogen, or $R^2$ is hydrogen, or $R^3$ is hydrogen. In some embodiments, $R^2$ and $R^3$ are each hydrogen.

In some embodiments, the compositions comprise a compound, tautomer or salt of Formula I, in which $R^4$ and $R^5$ are alkoxy, and in more specific embodiments, $R^4$ and $R^5$ are methoxy. In other embodiments, the compositions comprise a compound, tautomer or salt of Formula I, in which $R^1$, $R^2$ and $R^4$ are alkoxy, and in more specific embodiments, $R^1$, $R^2$ and $R^4$ are methoxy.

In some embodiments, the compositions comprise a compound, tautomer or salt of Formula I, in which $R^6$ and $R^7$ are alkyl, and in more specific embodiments $R^6$ and $R^7$ are each methyl. In still more specific embodiments, $R^6$ and $R^7$ are each methyl and $R^8$ is hydrogen.

In some embodiments, the compositions comprise a compound, tautomer or salt of Formula I, in which $R^6$ is halogen and $R^7$ is hydrogen, and in more specific embodiments, $R^6$ is chlorine and $R^7$ is hydrogen. In still more specific embodiments, $R^6$ is chlorine and $R^7$ and $R^8$ are hydrogen.

In some embodiments, the compositions comprise a compound, tautomer or salt of Formula I, in which $R^9$ is alkyl, and in more specific embodiments, $R^9$ is methyl.

In some embodiments, the compositions comprise a compound, tautomer or salt of Formula I, in which $R^9$ is optionally substituted acylphenyl, and in more specific embodiments, $R^9$ is acylphenyl or acyl(4-fluorophenyl).

In some embodiments, the compositions comprise a compound or salt of Formula II, in which $R^{10}$ is optionally substituted aryl, and in more specific embodiments, $R^{10}$ is optionally substituted phenyl, or $R^{10}$ is tolyl. In more specific embodiments, $R^{10}$ is p-tolyl. In still more specific embodiments, $R^{10}$ is p-tolyl, $R^{11}$ is phenyl, $R^{12}$ is allyl, and Z is a bond; or $R^{10}$ is phenyl, $R^{11}$ is 2-thienyl, $R^{12}$ is 2-methylcyclohexyl, and Z is a bond.

In some embodiments, the compositions comprise a compound or salt of Formula II, in which $R^{10}$ is alkyl or optionally substituted alkyl, and in more specific embodiments, $R^{10}$ is methyl. In still more specific embodiments, $R^{10}$ is methyl and $R^{11}$ is 2-chlorophenyl. In yet still more specific embodiments, $R^{10}$ is methyl, $R^{11}$ is 2-chlorophenyl, $R^{12}$ is ethoxy, and Z is $C_2$ alkyl; or $R^{10}$ is methyl, $R^{11}$ is 2-chlorophenyl, $R^{12}$ is tetrahydrofuran-2-yl, and Z is $C_2$ alkyl; or $R^{11}$ is methyl, $R^{11}$ is 2-chlorophenyl, $R^{12}$ is tetrahydrothiopyran-4-yl, and Z is a bond.

In some embodiments, the compositions comprise a compound or salt of Formula II, in which $R^{11}$ is optionally substituted aryl, and in more particular embodiments $R^{11}$ is phenyl or halophenyl. In more specific embodiments, $R^{11}$ is chlorophenyl, and in yet still more specific embodiments, $R^{11}$ is 2-chlorophenyl.

In some embodiments, the compositions comprise a compound or salt of Formula II, in which $R^{11}$ is optionally substituted heteroaryl, and in more specific embodiments $R^{11}$ is thienyl. In still more specific embodiments, $R^{11}$ is 2-thienyl.

In some embodiments, the compositions comprise a compound or salt of Formula II, in which $R^{12}$ is optionally substituted, fully saturated cycloalkyl, and in more specific embodiments, $R^{12}$ is optionally substituted, fully saturated $C_3$-$C_6$ cycloalkyl. In still more specific embodiments, $R^{12}$ is 2-methylcyclohexyl, and in yet still more specific embodiments, $R^{12}$ is 2-methylcyclohexyl and Z is a bond.

In some embodiments, the compositions comprise a compound or salt of Formula II, in which $R^{12}$ is optionally substituted heterocycloalkyl, and in more specific embodiments, $R^{12}$ is tetrahydrofuranyl or tetrahydrothiopyranyl. In still more specific embodiments, $R^{12}$ is tetrahydrofuran-2-yl, and Z is $C_2$ alkyl; or $R^{12}$ is tetrahydro-2H-thiopyran-4-yl and Z is a bond.

In some embodiments, the compositions comprise a compound or salt of Formula II, in which $R^{12}$ is alkenyl, and in more specific embodiments, $R^{12}$ is allyl. In still more specific embodiments, $R^{12}$ is allyl and Z is a bond.

In some embodiments, the compositions comprise a compound or salt of Formula II, in which $R^{12}$ is alkoxy, and in more specific embodiments, $R^{12}$ is ethoxy. In still more specific embodiments, $R^{12}$ is ethoxy and Z is $C_2$ alkyl.

In some embodiments, the compositions comprise a compound or salt of Formula II, in which Z is $C_1$-$C_6$ alkyl, and in some embodiments, Z is $C_1$-$C_3$ alkyl. In more specific embodiments, Z is a straight-chain, saturated alkylene moiety, specifically a divalent methylene, ethylene, propylene, butylene, pentylene, or hexylene moiety.

In some embodiments, the compositions comprise a compound or salt of Formula II in which Z is a bond. As used herein, the term "bond" refers to a direct attachment between the amide nitrogen atom of Formula II and the moiety comprising $R^{12}$. That is, in embodiments, wherein a bond exists between the amide nitrogen atom and $R^{12}$, there is/are no intervening bridging atom(s).

In non-limiting embodiments, examples of specific compounds meeting the structural requirements of Formulas I and II that can be suitable for use in the various embodiments of the present disclosure include:

Formula I-i: 2-mesityl-4,5-diphenyl-H-imidazole

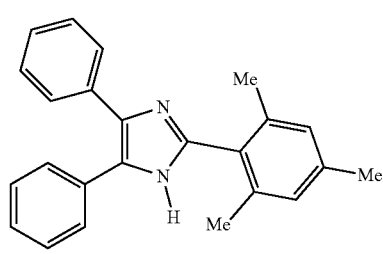

Formula I-i

Formula I-ii: 2-(2,6-dichlorophenyl)-4-(2,5-dimethylphenyl)-5-phenyl-1H-imidazole

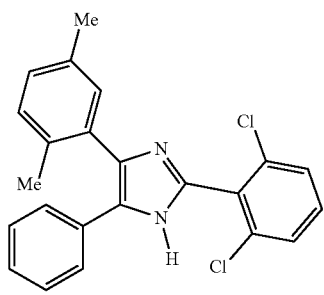

Formula I-iii: 2-(2-chloro-6-fluorophenyl)-4-(2,5-dimethylphenyl)-5-phenyl-1H-imidazole

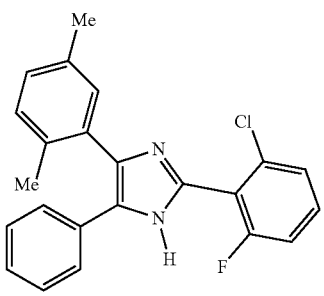

Formula I-iv:
2-(2,4-dimethoxyphenyl)-4,5-diphenyl-1H-imidazole

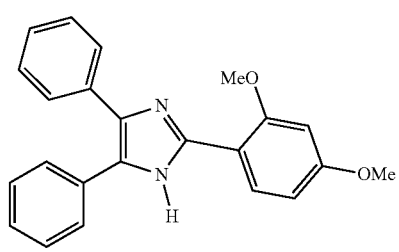

Formula I-v:
2-(2-ethoxyphenyl)-4,5-diphenyl-1H-imidazole

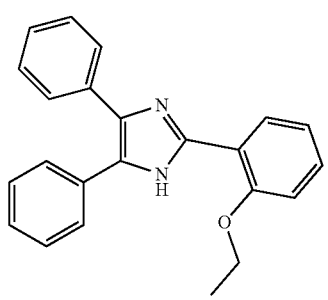

Formula I-vi: 4,5-diphenyl-2-(2-(prop-2-yn-1-yloxy)phenyl)-1H-imidazole

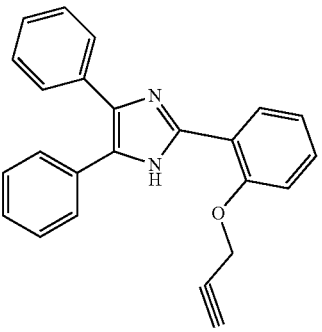

Formula I-vii: 5-(3-chlorophenyl)-2-(2,4-dichlorophenyl)-4-phenyl-1H-imidazole

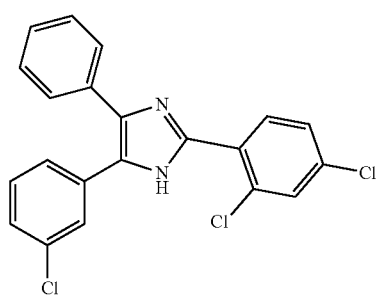

Formula I-vi ii: 4,5-diphenyl-2-(2,3,4-trimethoxyphenyl)-1H-imidazole

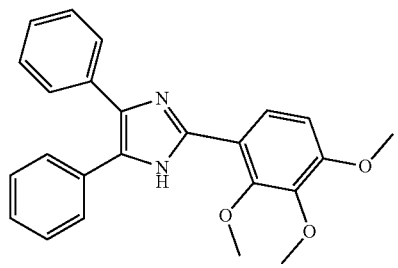

Formula I-ix: 2-(4-(methylthio)phenyl)-4,5-di-p-tolyl-1H-imidazole

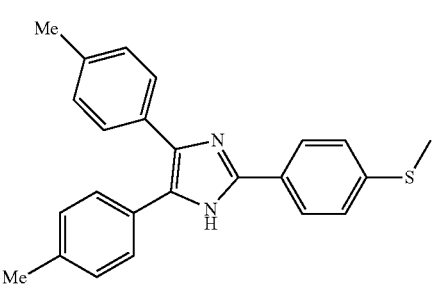

Formula I-x: (4-fluorophenyl)(4-(2-(3-fluorophenyl)-5-phenyl-1H-imidazol-4-yl)phenyl)methanone Formula I-x

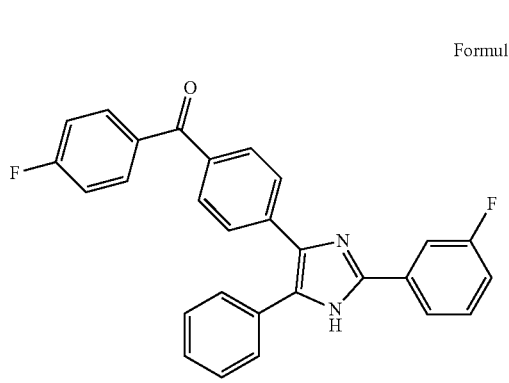

Formula II-i: N-allyl-3-phenyl-1-(p-tolyl)-1H-pyrazole-4-carboxamide

Formula II-i

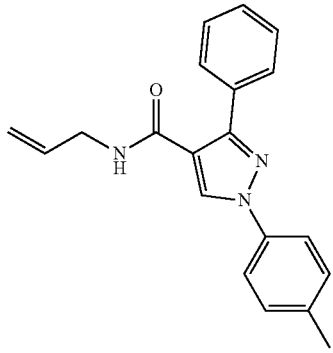

Formula II-ii: N-(2-methylcyclohexyl)-1-phenyl-3-(thiophen-2-yl)-1H-pyrazole-4-carboxamide Formula II-ii

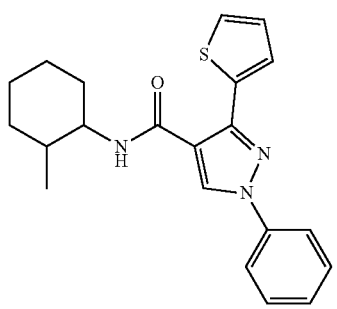

Formula II-iii: 3-(2-chlorophenyl)-N-(2-ethoxyethyl)-1-methyl-1H-pyrazole-4-carboxamide Formula II-iii

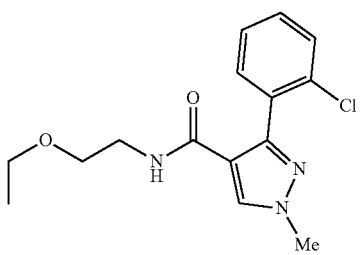

Formula II-iv: 3-(2-chlorophenyl)-1-methyl-N-(2-tetrahydrofuran-2-yl)ethyl)-1H-pyrazole 4-carboxamide, and Formula II-iv

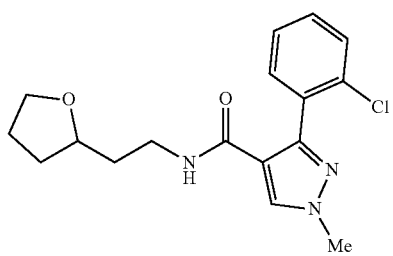

Formula II-v: 3-(2-chlorophenyl)-1-methyl-N-(tetrahydro-2H-thiopyran-4-yl)-1H-pyrazole-4-carboxamide Formula II-v

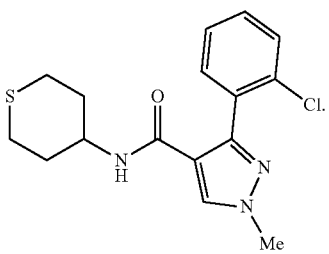

Also presented herein are compositions comprising an effective amount of a compound of Formula I, Formula II or a mixture thereof for administration to a plant, a seed, soil or an insect to control insect pests. Methods employing a composition containing an effective amount of such compounds are also expressly described herein. It is to be recognized that an effective amount of a compound of Formula I and/or Formula II may differ depending upon how the compositions are being applied. For example, applying the compositions to a plant may entail a different effective amount than when the compositions are applied directly to an insect. In another example, effective amounts of a compound of Formula I or Formula II may vary for different types of insects. Furthermore, it is to be recognized that an effective amount of the compound of Formula I and/or Formula II may represent a quantity that is sufficient to kill a certain type of insect pest. However, it is to be recognized that in some alternative embodiments, an effective amount may represent a quantity that is sufficient to drive an insect pest away from a target area and/or prevent the insect pest from reproducing, for example.

Particular compounds, tautomers or salts that may be present in an effective amount within compositions of the present disclosure include, for example, compounds of Formulas I-i through I-x and II-i through II-v.

Compositions of the present disclosure may be chosen from a number of formulation types including but not limited to, soluble concentrates, suspension concentrates, oil miscible liquids, ultra-low volume liquids, emulsifiable concentrates, dispersible concentrates, microemulsions, emulsions (both oil-in-water and water-in-oil), oil dispersions, capsule suspensions, and microencapsulated particles. Other examples include dry compositions, including but not limited to, dustable powders, soluble powders, water-soluble granules, wettable powders, water-dispersible granules, spreadable granules and seed treatments.

The compositions described herein can comprise any adjuvants, excipients, or other desirable component known in the art. Non-limiting examples of additional ingredients include surfactants, co-surfactants, permeation enhancers, dispersants, wetting agents and co-solvents.

Compositions described herein may further comprise a surfactant in some embodiments. Suitable surfactants can include those that promote dispersion of the compound of Formula I or Formula II in a liquid phase. Surfactants can be chosen for compatibility with a particular application and compound. Suitable surfactants can be chosen from cationic surfactants, anionic surfactants, zwitterionic surfactants, and neutral surfactants, and illustrative examples of each category will be familiar to one having ordinary skill in the art.

In additional embodiments, the compositions described herein may further comprise an additional co-active. The co-active may be, for example, an insecticide, a fungicide, an herbicide, a nematicide, a biocontrol agent, a microorganism, or any mixture thereof. Suitable examples of these additional co-actives are provided hereinafter.

Non-limiting examples of insecticides and nematicides include carbamates, diamides, macrocyclic lactones, neonicotinoids, organophosphates, phenylpyrazoles, pyrethrins, spinosyns, synthetic pyrethroids, tetronic and tetramic acids. For example, a liquid seed treatment composition may comprise one or more insecticides and nematicides selected from abamectin, aldicarb, aldoxycarb, bifenthrin, carbofuran, chlorantraniliprole, clothianidin, cyantraniliprole, cyfluthrin, cyhalothrin, cypermethrin, deltamethrin, dinotefuran, emamectin, ethiprole, fenamiphos, fipronil, flubendiamide, fosthiazate, imidacloprid, ivermectin, lambda-cyhalothrin, milbemectin, tioxazafen, nitenpyram, oxamyl, permethrin, spinetoram, spinosad, spirodichlofen, spirotetramat, tefluthrin, thiacloprid, thiamethoxam, tioxazafen, and thiodicarb.

Non-limiting examples of useful fungicides include aromatic hydrocarbons, benzimidazoles, benzothiadiazole, carboxamides, carboxylic acid amides, morpholines, phenylamides, phosphonates, quinone outside inhibitors (e.g., strobilurins), thiazolidines, thiophanates, thiophene carboxamides, and triazoles. Non-limiting examples of fungicides include acibenzolar-S-methyl, azoxystrobin, benalaxyl, bixafen, boscalid, carbendazim, chlorothalonil, cyproconazole, dimethomorph, epoxiconazole, fludioxonil, fluopyram, fluxapyroxad, fluoxastrobin, flutianil, flutolanil, fluxapyroxad, fosetyl-Al, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thiabendazole, thifluzamide, thiophanate, tolclofos-methyl, trifloxystrobin, and triticonazole.

Non-limiting examples of herbicides include ACCase inhibitors, acetanilides, AHAS inhibitors, carotenoid biosynthesis inhibitors, EPSPS inhibitors, glutamine synthetase inhibitors, PPO inhibitors, PS II inhibitors, and synthetic auxins. Particular examples of herbicides include acetochlor, clethodim, dicamba, flumioxazin, fomesafen, glyphosate, glufosinate, mesotrione, quizalofop, saflufenacil, sulcotrione, and 2,4-D (2,4-dichlorophenoxyacetic acid).

Additional co-actives may also comprise substances such as, biological control agents, microbial extracts, natural products, plant growth activators or plant defense agents. Non-limiting examples of biological control agents include bacteria, fungi, beneficial nematodes, and viruses.

In certain embodiments, the biological control agent can comprise a bacterium of the genus *Actinomycetes, Agrobacterium, Arthrobacter, Alcaligenes, Aureobacterium, Azobacter, Bacillus, Beijerinckia, Bradyrhizobium, Brevibacillus, Burkholderia, Chromobacterium, Clostridium, Clavibacter, Comamonas, Corynebacterium, Curtobacterium, Enterobacter, Flavobacterium, Gluconobacter, Hydrogenophaga, Klebsiella, Metarhizium, Methylobacterium, Paenibacillus, Pasteuria, Photorhabdus, Phyllobacterium, Pseudomonas, Rhizobium, Serratia, Sphingobacterium, Stenotrophomonas, Streptomyces, Variovorax,* and *Xenorhabdus*. In particular embodiments the bacteria is selected from the group consisting of *Bacillus amyloliquefaciens, Bacillus cereus, Bacillus firmus, Bacillus, lichenformis, Bacillus pumilus, Bacillus sphaericus, Bacillus subtilis, Bacillus thuringiensis, Bradyrhizobium japonicum, Chromobacterium subtsugae, Metarhizium anisopliae, Pasteuria nishizawae, Pasteuria peneirans, Pasteuria usage, Pseudomonas fluorescens,* and *Streptomyces lydicus*.

In certain embodiments, the biological control agent can comprise a fungus of the genus *Alternaria, Ampelomyces, Aspergillus, Aureobasidium, Beauveria, Colletotrichum, Coniothyrium, Gliocladium, Metarhizium, Muscodor, Paecilomyces, Penicillium, Trichoderma, Typhula, Ulocladium,* and *Verticillium*. In another embodiment, the fungus is *Beauveria bassiana, Coniothyrium minilans, Gliocladium virens, Muscodor albus, Paecilomyces lilacinus, Penicillium bilaiae, Trichoderma asperellum, Trichoderma polysporum,* or *Trichoderma virens*.

In certain embodiments, the biological control agent can comprise harpin, *Reynoutria sachalinensis*, jasmonate, lipochitooligosaccharides, salicylic acid and/or isoflavones. In another embodiment, the biological control agent may comprise *Bacillus firmus*.

Compounds and compositions described herein can be administered to seeds, plants or the growth medium of plants (e.g., soil), wherein the control of insects is desired. The compounds and compositions can likewise be administered directly to insects for similar purposes. For example, in various embodiments, the present disclosure provides methods of controlling insect pests, in which the methods comprise administering to a plant, seed, soil or insect, a composition comprising an effective amount of a compound described herein.

More specifically, in some embodiments, methods described herein may comprise administering to a plant, seed, soil or insect, a composition comprising a compound of Formula I, a tautomer thereof, or a salt thereof, where the variables in Formula I are defined as above. In some or other embodiments, methods described herein may comprise administering to a plant, seed, soil or insect, a composition comprising a compound of Formula II or a salt thereof, where the variables in Formula II are defined as above.

The techniques by which the compositions are administered to a plant, seed, soil and/or insect are not believed to be particularly limited. Particular techniques can be chosen depending upon the target to which the compositions are to be administered. Suitable techniques can include, for example, spreading a solid formulation or spraying a liquid formulation of the compositions in the case of administration to a plant or insect. In the case of administration to a seed, the compositions may be blended with a plurality of seeds in a hopper, or a liquid formulation may be sprayed upon a plurality of seeds, for example.

In some embodiments, the compositions can be administered to a seed. In other embodiments, the compositions can be administered to a plant. In more particular embodiments, the compositions can be administered to foliage of a plant or to soil surrounding a root zone of the plant. In still other embodiments, the compositions can be administered directly to an insect. Choice of administration in a given manner can be dictated whether the insects are primarily surface insects or sub-surface insects, for example.

Non-limiting examples of plants that may be protected from insect pests in accordance with the methods described herein include monocotyledon crops such as corn, wheat, barley, rye, sugar cane, rice, sorghum, oat; dicotyledon crops such as cotton, sugar beet, peanut, potato, sweet potato, yam sunflower, soybean, alfalfa, flax, canola, grapes, tobacco; vegetables including *Solanaceae* vegetables such as eggplant, tomato, green pepper and pepper; *Cucurbitaceae* vegetables such as cucumber, pumpkin, zucchini, watermelon, melon, and squash; *Brassicaceae* vegetables such as radish, turnip, horseradish, Chinese cabbage, cabbage, leaf mustard, broccoli and cauliflower; *Asteraceae* vegetables such as artichoke and lettuce; *Liliaceae* vegetables such as leek, onion, garlic, and asparagus; *Apiaceae* vegetables such as carrot, parsley, celery and parsnip; *Chenopodiaceae* vegetables such as spinach and chard; Lamiaceae vegetables such as mint and basil; flowers such as *petunia*, morning glory, carnation, *chrysanthemum* and rose; foliage plants; fruit trees such as pome fruits (e.g., apple, pear and Japanese pear), stone fruits (e.g., peach, plum, nectarine, cherry, apricot, and prune), citrus (e.g., orange, lemon, lime and grapefruit), tree nuts (e.g., chestnut, pecan, walnut, hazel, almond, pistachio, cashew, and macadamia), berries such as blueberry, cranberry, blackberry, strawberry, and raspberry; persimmon; olive; loquat; banana; coffee; palm; cocoa; the other trees such as tea, mulberry, flower trees, and landscape trees (e.g., ash, birch, dogwood, *eucalyptus*, ginkgo, lilac, maple, oak, poplar, *Formosa* sweet gum, sycamore, fir, hemlock fir, needle juniper, pine, spruce, and yew); and turf.

Non-limiting examples of insect pests that may be controlled by the methods described herein include members of the orders Coleoptera, Diptera, Hemiptera, and Lepidoptera.

Non-limiting examples of the members of the order Coleoptera include *Acalymma, Acanthoscelides, Adoretus, Agelasica, Agriotes, Alphitobius, Amphimallon, Anobium, Anoplophora, Anthononius, Anthrenus, Apion, Apogonia, Atomaria, Attagenus, Bruchidius, Bruchus, Cassida, Cerotoma, Ceutorrhynchus, Chaetocnema, Cleonus, Conoderus, Cosmopolites, Costelytra, Ctenicera, Curculio, Cryptorhynchus, Cylindrocopturus, Dermestes, Diabrotica, Dichocrocis, Diloboderus, Epilachna, Epitrix, Faustinus, Gibbium, Hellula, Heteronychus, Heteronyx, Hylamorpha, Hylotrupes, Hypera, Hypothenemus, Lachnosterna, Lema, Leptinotarsa, Leucoptera, Lissorhoptrus, Lixus, Luperodes, Lyctus, Megascelis, Melanotus, Meligethes, Melolontha, Migdolus, Monochanus, Naupactus, Niptus, Oryctes, Oryzaephilus, Oryzaphagus, Oliorrhynchus, Oxycetonia, Phaedon, Phyllophaga, Phyllotreta, Popillia, Premnotrypes, Prostephanus, Psylliodes, Ptinus, Rhizobius, Rhizopertha, Sitophilus, Sphenophorus, Stegobium, Sternechus, Symphyletes, Tanymecus, Tenebrio, Tribolium, Trogoderma, Tychius, Xylotrechus*, and *Zabrus*.

Non-limiting examples of the members of the order Diptera include *Aedes, Agromyza, Anastrepha, Anopheles, Asphondylia, Bactrocera, Bibio, Calliphora, Ceratitis, Chironomus, Chrysomyia, CHrysops, Cochliomyia, Contarinia, Cordylobia, Culex, Culicoides, Culiseta, Cuterebra, Dacus, Dasyneura, Delia, Dermatobia, Drosophila, Echinocnemus, Fannia, Gasterophilus, Glossina, Haematopota, Hydrellia, Hylemyia, Hyppobosca, Hypoderma, Liriomyza, Lucilia, Lutzomia, Mansonia, Musca, Nezara, Oestrus, Oscinella, Pegomyia, Phlebotomus, Phorbia, Phormia, Prodiplosis, Psila, Rhagoletis, Sarcophaga, Simulium, Stomoxys, Tabanus, Tannia, Tetanops*, and *Tipula*.

Non-limiting examples of the members of the order Hemiptera (sub-order Heteroptera) include *Anasa tristis, Antestiopsis* spp., *Boisea* spp., *Blissus* spp., *Calocoris* spp., *Campylomma livida, Cavelerius* spp., *Cimex* spp., *Cimex lectularius, Cimex hemipterus, Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psalhlus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

Non-limiting examples of the members of the order Homoptera include *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyaloplerus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

Non-limiting examples of the members of the order Lepidoptera include *Acronicta major, Adoxophyes, Aedia leucomelas, Agrotis, Alabama, Amyelois transitclla, Anarsia, Anticarsia, Argyroploce, Barathra brassicae, Borbo cinnara, Bucculatrix thurberiella, Bupalus piniarius, Busseola, Cacoecia, Caloptilia theivora, Capua reticulana, Carpocapsa pomonella, Carposina niponensis, Chematobia brumata, Chilo, Choristoneura, Clysia ambiguella, Cnaphalocerus, Cnephasia, Conopomorpha, Conotrachelus, Copitarsia, Cydia, Dalaca noctuides, Diaphania, Diatraea saccharalis, Earias, Ecdytolopha aurantium, Elasmopalpus lignosellus, Eldana saccharina, Ephestia, Epinotia, Epiphyas postvittana, Etiella, Eulia, Eupoecilia ambiguella, Euproctis, Euxoa, Feltia, Galleria mellonella, Gracillaria, Grapholitha, Hedylepta, Helicoverpa, Heliothis, Hofmannophila pseudospretella, Homoeosoma, Homona, Hyponomeuta padella, Kakivoria flavofasciata, Laphygma, Laspeyresia molesta, Leucinodes orbonalis, Leucoptera, Lithocolletis, Lithophane antennata, Lobesia, Loxagrotis albicosta, Lymantria, Lyonetia, Malacosoma neustria, Maruca testulalis, Mamestra brassicae, Mocis, Mythimna separata, Nymphula, Oiketicus, Oria, Orthaga, Ostrinia, Oulema oryzae, Panolis flammea, Parnara, Pectinophora, Perileucoptera, Phthorimaea, Phyllocnistis citrella, Phyllonorycter, Pieris, Platynota stultana, Plodia interpunctella, Plusia, Plutella xylostella, Prays, Prodenia, Protoparce, Pseudaletia, Pseudoplusia includens, Pyrausta nubilalis, Rachiplusia nu, Schoenobius, Scirpophaga, Scotia segetum, Sesamia, Sparganothis, Spodoptera, Stathmopoda, Stomopteryx subsecivella, Synanthedon, Tecia solanivora, Thermesia gemmatalis, Tinea pellionella, Tineola bisselliella, Tortrix, Trichophaga tapetzella, Trichoplusia, Tuta absoluta,* and *Virachola.*

In more specific embodiments, illustrative insect pests that can be controlled by practicing the disclosure herein include, for example, diamondback moth, fall armyworm, soybean looper, Western corn rootworm, Western tarnished plantbug and yellow fever mosquito.

Non-limiting examples of plants that can be protected from insect pests according to the disclosure herein include crop plants. Illustrative crop plants that can be protected according to the disclosure herein include, for example, corn, cotton, soybeans, cereals, peanuts, sunflower, dry beans, peas, legume vegetables, sugarcane, alfalfa, and canola. Ornamental plants can be protected in a similar manner.

In some embodiments, the disclosure is related to a seed that has been treated with a composition as described herein comprising a compound, tautomer or salt of Formula I and/or a compound or salt of Formula II. The compound of Formula I and/or Formula II becomes associated with the resulting treated seed. The treated seed can promote distribution of the compound of Formula I and/or Formula II into the root zone surrounding the plant upon being planted. In some embodiments, the compositions can be administered to a seed using a seed treatment such as, for example, solid matrix priming, imbibition, coating, and spraying. The treated seed may be for any plant species as described herein. In some embodiments, a seed can be treated with a composition as described herein, including formulating, mixing in a seed treater tank, or combining on a seed by overcoating one or more additional active ingredients. The active ingredient(s) may be, for example, an insecticide, a fungicide, an herbicide, a nematicide, a biological control agent or a microorganism. The seed may also be a transgenic seed in some embodiments.

Embodiments disclosed herein include:

Embodiment A

A method for controlling insect pests. The methods comprise: administering to a plant, seed, soil or insect, a composition comprising a compound of Formula I, a tautomer thereof or a salt thereof

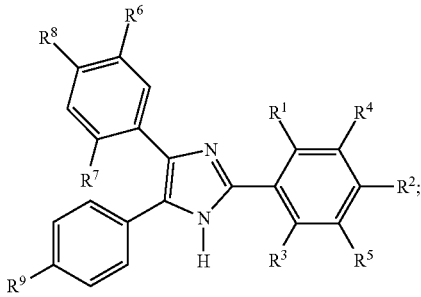

Formula I wherein $R^1$, $R^2$ and $R^3$ are independently selected from the group consisting of hydrogen, halogen, alkyl, alkoxy, thioalkyl, alkenyloxy, alkynyloxy, haloalkyl and haloalkoxy; wherein $R^4$ and $R^5$ are independently selected from the group consisting of hydrogen, halogen, alkyl, alkoxy, alkenyloxy and alkynyloxy; wherein at least one of $R^1$-$R^5$ is not hydrogen; wherein $R^6$ and $R^7$ are independently selected from the group consisting of hydrogen, halogen and alkyl; wherein $R^8$ is selected from the group consisting of hydrogen, alkyl and optionally substituted acylphenyl; and wherein $R^9$ is selected from the group consisting of hydrogen and alkyl.

Embodiment B

A method for controlling insect pests. The methods comprise: administering to a plant, seed, soil or insect, a composition comprising a compound of Formula II or a salt thereof

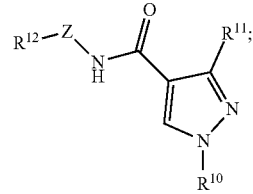

Formula II wherein $R^{10}$ is selected from the group consisting of optionally substituted aryl and optionally substituted alkyl; wherein $R^{11}$ is selected from the group consisting of optionally substituted aryl and optionally substituted heteroaryl; wherein $R^{12}$ is selected from the group consisting of optionally substituted alkyl, optionally substituted alkenyl, optionally substituted alkynyl, optionally substituted alkoxy, optionally substituted heterocycloalkyl and optionally substituted, fully saturated cycloalkyl; and wherein Z is $C_1$-$C_6$ alkyl or a bond.

Embodiment C

An insecticidal treatment composition. The treatment compositions comprise: a compound of Formula I, a tautomer thereof or a salt thereof

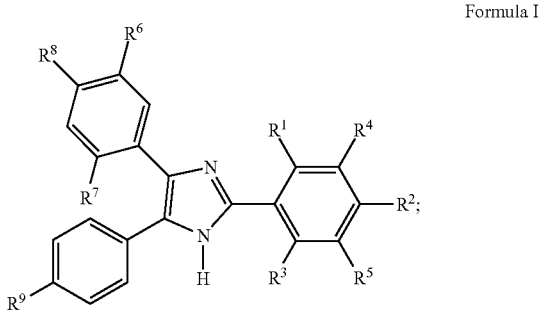

Formula I wherein $R^1$, $R^2$ and $R^3$ are independently selected from the group consisting of hydrogen, halogen, alkyl, alkoxy, thioalkyl, alkenyloxy, alkynyloxy, haloalkyl and haloalkoxy; wherein $R^4$ and $R^5$ are independently selected from the group consisting of hydrogen, halogen, alkyl, alkoxy, alkenyloxy and alkynyloxy; wherein at least one of $R^1$-$R^5$ is not hydrogen; wherein $R^6$ and $R^7$ are independently selected from the group consisting of hydrogen, halogen and alkyl; wherein $R^8$ is selected from the group consisting of hydrogen, alkyl and optionally substituted acylphenyl; and wherein $R^9$ is selected from the group consisting of hydrogen and alkyl.

Embodiment D

A treated seed. The treated seeds comprise the compound of Formula I, a tautomer thereof, or a salt thereof.

Embodiment E

An insecticidal treatment composition. The treatment compositions comprise: a compound of Formula II or a salt thereof

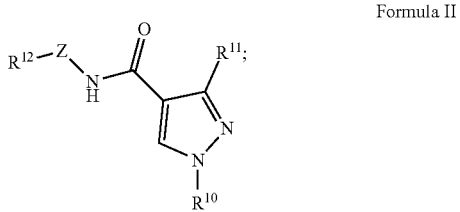

Formula II wherein $R^{10}$ is selected from the group consisting of optionally substituted aryl and optionally substituted alkyl; wherein $R^{11}$ is selected from the group consisting of optionally substituted aryl and optionally substituted heteroaryl; wherein $R^{12}$ is selected from the group consisting of optionally substituted alkyl, optionally substituted alkenyl, optionally substituted alkynyl, optionally substituted alkoxy, optionally substituted heterocycloalkyl and optionally substituted, fully saturated cycloalkyl; and wherein Z is $C_1$-$C_6$ alkyl or a bond.

Embodiment F

A treated seed. The treated seeds comprise the compound of Formula II or a salt thereof.

Each of embodiments A-F may have one or more of the following additional elements in any combination:

Element 1: wherein $R^1$, $R^2$ and $R^3$ are independently selected from the group consisting of hydrogen, halogen, alkyl, alkoxy, thioalkyl and alkynyloxy.

Element 2: wherein an effective amount of a compound selected from the group consisting of 2-mesityl-4,5-diphenyl-1H-imidazole, 2-(2,6-dichlorophenyl)-4-(2,5-dimethylphenyl)-5-phenyl-1H-imidazole, 2-(2-chloro-6-fluorophenyl)-4-(2,5-dimethylphenyl)-5-phenyl-1H-imidazole, 2-(2, 4-dimethoxyphenyl)-4,5-diphenyl-1H-imidazole, 2-(2-ethoxyphenyl)-4,5-diphenyl-1H-imidazole, 4,5-diphenyl-2-(2-(prop-2-yn-1-yloxy)phenyl)-1H-imidazole, 5-(3-chlorophenyl)-2-(2,4-dichlorophenyl)-4-phenyl-1H-imidazole, 4,5-diphenyl-2-(2,3,4-trimethoxyphenyl)-1H-imidazole, 2-(4-(methylthio)phenyl)-4,5-di-p-tolyl-1H-imidazole, (4-fluorophenyl)(4-(2-(3-fluorophenyl)-5-phenyl-1H-imidazol-4-yl)phenyl) methanone, a tautomer thereof and a salt thereof is administered to the plant, seed, soil or insect.

Element 3: wherein the composition is administered to a seed.

Element 4: wherein the composition is administered to a plant.

Element 5: wherein the composition is applied to foliage of the plant.

Element 6: wherein the composition is applied to soil surrounding a root zone of the plant.

Element 7: wherein the plant is a crop plant selected from the group consisting of corn, cotton, soybeans, cereals, peanuts, sunflower, dry beans, peas, legume vegetables, sugarcane, alfalfa and canola.

Element 8: wherein the insect pest is a member of an order selected from the group consisting of Coleoptera, Diptera, Hemiptera and Lepidoptera.

Element 9: wherein the insect pest is a member of a genus selected from the group consisting *Aedes, Diabrotica, Lygus, Plutella, Pseudoplusia* and *Spodoptera.*

Element 10: wherein the insect pest is selected from the group consisting of diamondback moth, fall armyworm, soybean looper, Western corn rootworm and yellow fever mosquito.

Element 11: wherein the treatment composition further comprises a surfactant.

Element 12: wherein the treatment composition further comprises a fungicide, an insecticide, a nematicide, an herbicide, a microorganism or mixtures thereof.

Element 13: wherein $R^{10}$ is selected from the group consisting of phenyl and tolyl, and $R^{11}$ is selected from the group consisting of phenyl, thienyl and chlorophenyl.

Element 14: wherein $R^{12}$ is selected from the group consisting of allyl, 2-methylcyclohexyl, ethoxy, tetrahydrofuran-2-yl, tetrahydro-2H-thiopyran-4-yl, and Z is $C_1$-$C_3$ alkyl or a bond.

Element 15: wherein an effective amount of a compound selected from the group consisting of N-allyl-3-phenyl-1-(p-tolyl)-1H-pyrazole-4-carboxamide, N-(2-methylcyclohexyl)-1-phenyl-3-(thiophen-2-yl)-1H-pyrazole-4-carboxamide, 3-(2-chlorophenyl)-N-(2-ethoxyethyl)-1-methyl-1H-pyrazole-4-carboxamide, 3-(2-chlorophenyl)-1-methyl-N-(2-(tetrahydrofuran-2-yl)ethyl)-1H-pyrazole-4-carboxamide, 3-(2-chlorophenyl)-1-methyl-N-(tetrahydro-2H-thiopyran-4-yl)-1H-pyrazole-4-carboxamide, and a salt thereof is administered to the plant, seed, soil or insect.

Having described the disclosure in detail, it will be apparent that modifications and variations are possible without departing from the scope of the claims. The following examples are to be considered as merely illustrative, and are not intended to limit the scope of this invention.

EXAMPLES

Generally, compounds of Formula I and II may be prepared using an extension of methods known to those having ordinary skill in the art.

Example 1: Synthesis of Compounds of Formula I

Compounds of Formula I may be prepared as illustrated by the exemplary synthetic route shown in Scheme 1 below. 5-Bromoimidazoles 3 with a diverse set of substitutions can be prepared via a copper-catalyzed cycloamination reaction of 1,1-dibromoalkenes 1 with corresponding amidines 2. Tri-substituted imidazoles 5 can be prepared from corresponding 5-bromo imidazoles 3 via Suzuki-Miyaura cross-coupling with appropriate arylboronic acids 4 under the conditions described in Scheme 1. Following deprotection, compounds of Formula I result.

Scheme 1: Synthetic scheme for the preparation of compounds of Formula I

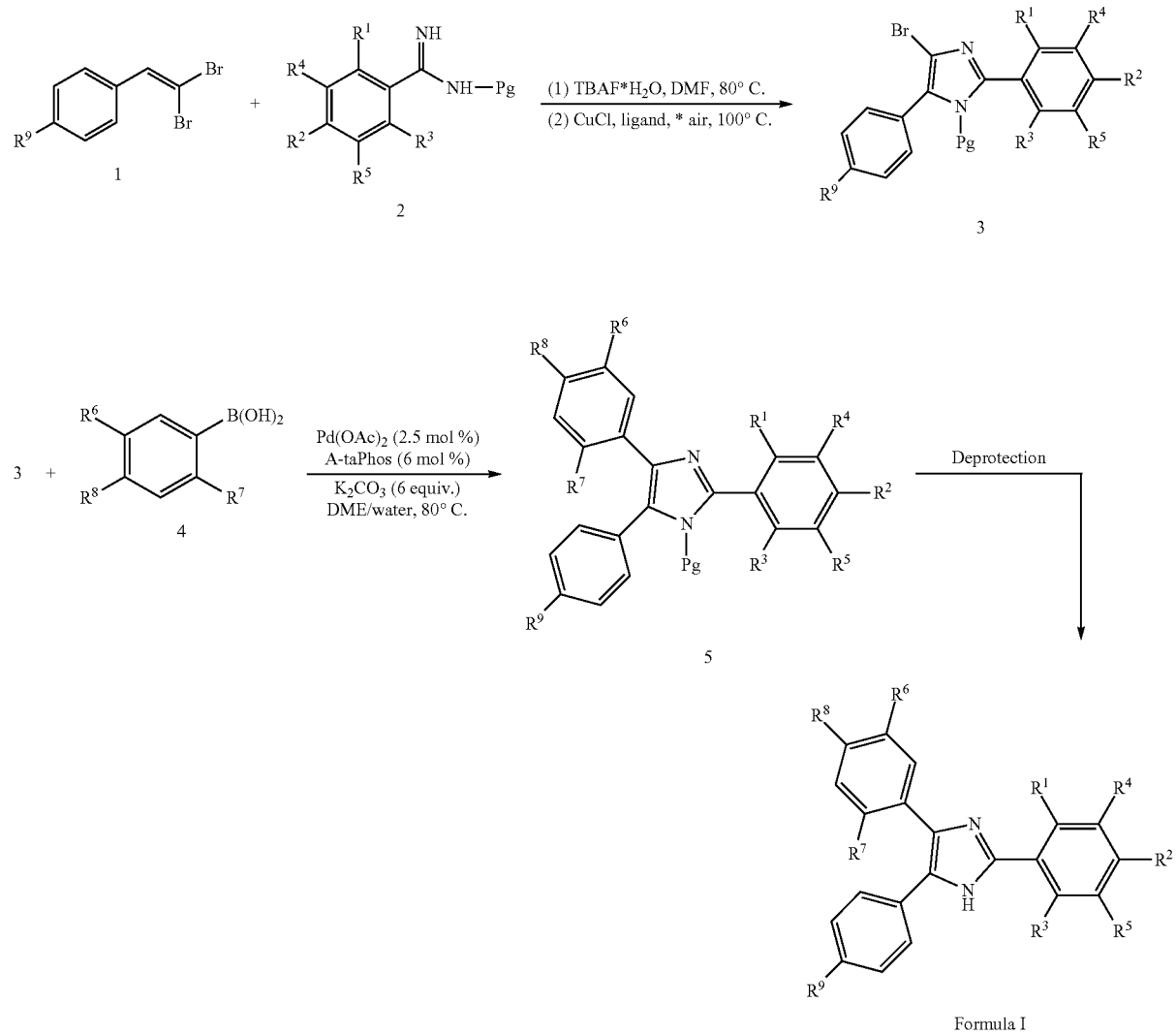

Ligand = 4,7-diphenyl-1,10-phenanthroline (20 mol %)
Pg = protecting group

Additionally, certain compounds of Formula I may also be prepared as generally set forth in Scheme 2 below. 2-aryl-4,5-dibromo imidazole 8 can be prepared via reaction of aryl aldehyde 6 with 1,2-ethanediamine followed by bromination of intermediate 7 with N-bromosuccinimide. The compounds of Formula I can be prepared from 4,5-dibromoimidazole 8 via Suzuki-Miyaura cross-coupling with arylboronic acid 9 as described in Scheme 2. As depicted in Scheme 2, arylboronic acid 9 is chosen such that compounds of Formula I with symmetrical substitution are formed (i.e., $R_8=R_9$ and $R_6=R_7=H$). Asymmetrical compounds of Formula I can be prepared by using differentially substituted arylboronic acids 9 (i.e., one arylboronic acid bearing the full range of $R^6$, $R^7$ and $R^8$ substitution and one arylboronic acid bearing $R^9$ substitution). When employing different arylboronic acids 9, differentially substituted regioisomers resulting from statistical reaction of arylboronic acids 9 with 4,5-dibromoimidazole 8 can result, which may need to be separated further.

Scheme 2: Synthetic Scheme for the preparation of compounds of Formula I

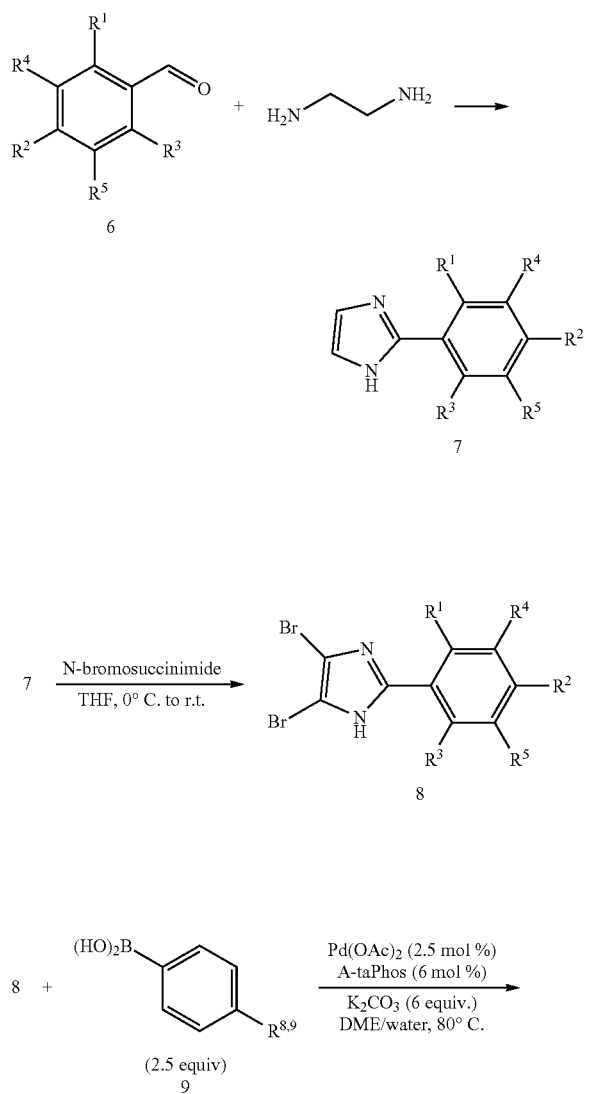

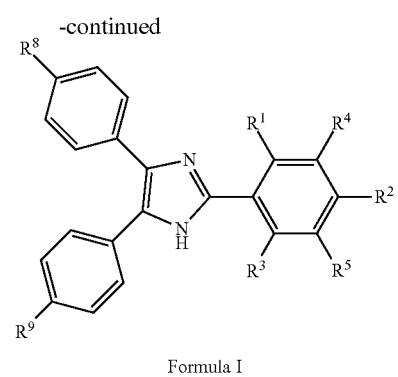

Formula I

Example 2: Synthesis of Compounds of Formula II

Compounds of Formula II can be prepared as illustrated by the exemplary reactions in Scheme 3. Intermediate pyrazole carbaldehyde 14 can be prepared by the reaction of aryl hydrazone 12 with Vilsmeier-Haack reagent (DMF/POCl$_3$). Oxidation of intermediate pyrazole carbaldehyde 14 with NaOCl$_2$ at 0° C. in the presence of a sulfamic acid scavenger furnished the corresponding acid 15. Aryl hydrazone 12 was prepared from the corresponding acetophenone, benzophenone or acylheteroaromatic derivative 10 and hydrazine 11 in ethanol in the presence of acetic acid. Compounds of Formula II can be prepared from the corresponding acid 15 and amine 16 using standard coupling reagents such as, for example, CDI or EDCI/HOBt in the presence of base (e.g, triethylamine).

Scheme 3: Synthetic Scheme for the preparation of compounds of Formula II

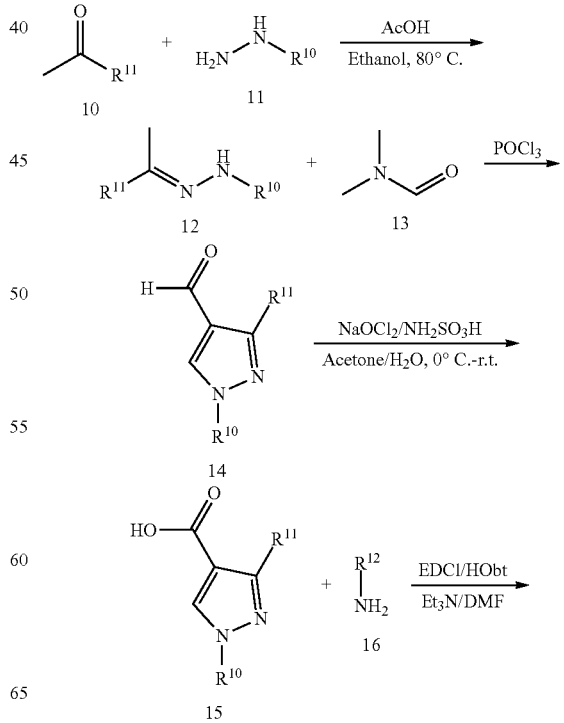

-continued

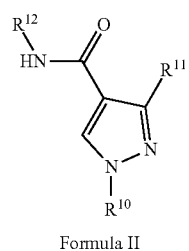

Formula II

Example 3: Insect Feeding Assays

For evaluating control of insect species, the test unit consisted of a 96-well bioassay plate filled with a species-specific artificial diet. Compounds were dissolved in DMSO and added as diet overlay to the indicated concentration, and dried/maintained overnight before infestation. Once dry, the bioassay plates were infested with a single neonate larva (nymph for lygus) per well. The bioassay plates were then held for 6 days in an incubator at 27° C. and 50% relative humidity. Sample response was then visually assessed based on mortality and stunting of the insect. A "+" score was given to samples which showed any level of stunting and/or mortality higher than that of the untreated controls. A "−" score was given to samples which showed no activity. Western corn rootworm data represents a summary of three replicates. Data for all other insect species represents a summary of two replicates. Summarized results are presented in the Tables below.

TABLE 1A

| Insect Feeding Assay—Western Corn Root Worm (WCR) | |
|---|---|
| Formula | WCR (0.1 mg/mL) |
| I-i | + |
| I-ii | + |
| I-iv | + |
| I-v | + |
| Untreated control (DMSO) | − |

TABLE 1B

| Insect Feeding Assay—Diamondback Moth (DBM) | |
|---|---|
| Formula | DBM (0.1 mg/mL) |
| II-i | + |
| II-ii | + |
| Untreated control (DMSO) | − |

TABLE 1C

| Insect Feeding Assay—Yellow Fever Mosquito (YFM) | |
|---|---|
| Formula | YEM (0.1 mginiL) |
| I-i | + |
| I-ii | + |
| I-iii | + |
| I-iv | + |

TABLE 1C-continued

| Insect Feeding Assay—Yellow Fever Mosquito (YFM) | |
|---|---|
| Formula | YEM (0.1 mginiL) |
| II-i | + |
| II-iii | + |
| II-iv | + |
| II-v | + |
| Untreated control (DMSO) | − |

Example 4: Insect Feeding Assays

For evaluating control of insect species in this example, the test unit consisted of a 96-well bioassay plate filled with species-specific artificial diet. Compounds were dissolved in DMSO and added as diet overlay to the indicated concentration and dried/maintained overnight before infestation. Once dry, the bioassay plates were infested with a single neonate larva (nymph for lygus) per well. The bioassay plates were held for 6 days in an incubator at 27° C. and 50% relative humidity. Each well was assessed for infestation and contamination. Wells that were contaminated or not infested were not included in the stunting and mortality assessment. A stunting score was reported based on the relative size of the survivors within the 8-well column with averaging across a 3 column replicate. Untreated control insects were used as a reference. Percent mortality was determined as the percentage of insects that did not survive the treatment with the compound divided by the total insect count within an 8-well column and averaged across a 3 column replicate. Under these assay conditions, "+" represents mortality or stunting significantly different compared to the untreated control and "−" represents no significant difference in mortality or stunting compared to the untreated control.

TABLE 2A

| Insect Feeding Assay—Diamondback Moth (DBM) | |
|---|---|
| Formula | DBM (0.05 mg/mL) |
| I-i | + |
| I-ii | + |
| I-iii | not tested |
| I-iv | + |
| I-v | − |
| I-vi | + |
| I-vii | + |
| I-viii | + |
| I-ix | + |
| I-x | + |
| II-i | + |
| II-ii | − |
| II-iii | − |
| II-iv | − |
| I-v | not tested |

TABLE 2B

| Insect Feeding Assay—Fall Armyworm (FAW) | |
|---|---|
| Formula | FAW (0.05 mg/mL) |
| I-i | − |
| I-ii | + |
| I-iii | not tested |
| I-iv | − |
| I-v | − |
| I-vi | − |

TABLE 2B-continued

Insect Feeding Assay—Fall Armyworm (FAW)

| Formula | FAW (0.05 mg/mL) |
|---|---|
| I-vii | + |
| I-viii | − |
| I-ix | + |
| I-x | + |
| I-i | − |
| II-ii | − |
| II-iii | − |
| II-iv | − |
| II-v | not tested |

TABLE 2C

Insect Feeding Assay—Soybean Looper (SL)

| Formula | SL (0.05 mg/mL) |
|---|---|
| I-i | − |
| I-ii | + |
| I-iii | not tested |
| I-iv | − |
| I-v | − |
| I-vi | − |
| I-vii | + |
| I-viii | − |
| I-ix | + |
| I-x | + |
| I-i | − |
| II-ii | − |
| II-iii | − |
| II-iv | − |
| II-v | not tested |

TABLE 2D

Insect Feeding Assay—Western Corn Rootworm (WCR)

| Formula | WCR (0.05 mg/mL) |
|---|---|
| I-i | not tested |
| I-ii | not tested |
| I-iii | not tested |
| I-iv | not tested |
| I-v | not tested |
| I-vi | not tested |
| I-vii | not tested |
| I-viii | + |
| I-ix | + |
| I-x | + |
| I-i | not tested |
| II-ii | not tested |
| II-iii | not tested |
| II-iv | not tested |
| II-v | not tested |

TABLE 2E

Insect Feeding Assay—Western Tarnished Plantbug

| Formula | WTP (0.05 mg/mL |
|---|---|
| I-i | − |
| I-ii | + |
| I-iii | not tested |
| I-iv | − |
| I-v | − |
| I-vi | + |
| I-vii | − |
| I-viii | − |
| I-ix | − |

TABLE 2E-continued

Insect Feeding Assay—Western Tarnished Plantbug

| Formula | WTP (0.05 mg/mL |
|---|---|
| I-x | + |
| I-i | − |
| II-ii | − |
| II-iii | − |
| II-iv | − |
| II-v | not tested |

TABLE 2F

Insect Feeding Assay—Yellow Fever Mosquito (YEW)

| Formula | YFM (0.05 mg/mL) |
|---|---|
| I-i | − |
| I-ii | + |
| I-iii | not tested |
| I-iv | + |
| I-v | − |
| I-vi | + |
| I-vii | + |
| I-viii | + |
| I-ix | − |
| I-x | − |
| I-i | − |
| II-ii | − |
| II-iii | − |
| II-iv | − |
| II-v | not tested |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is the following:

1. A method of controlling insect pests, the method comprising:
    administering to a plant, seed, soil or insect, a composition comprising a compound of Formula II or a salt thereof

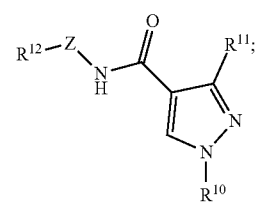

Formula II wherein $R^{10}$ is selected from the group consisting of phenyl, halophenyl, tolyl, napthyl, phenanthrenyl, anthracentyl, indenyl, azulenyl, biphenyl, biphenylenyl, and fluorenyl and $C_1$-$C_{10}$ alkyl;

wherein $R^{11}$ is selected from the group consisting of phenyl, halophenyl, tolyl, napthyl, phenanthrenyl, anthracentyl, indenyl, azulenyl, biphenyl, biphenylenyl, and fluorenyl and 5- to 14-membered heteroaryl;

wherein $R^{12}$ is selected from the group consisting of $C_1$-$C_{10}$ alkyl, $C_1$-$C_{10}$ alkenyl, $C_1$-$C_{10}$ alkynyl, $C_1$-$C_{10}$ alkoxy, cyclopropyl, cyclobutyl, cyclopentyl, cyclohexyl, methylcyclohexyl, cycloheptyl, azetidinyl, oxetanyl, tetrahydrofuranyl, dioxolinyl, pyrrolidinyl, pyrrolidinonyl, imidazolidinyl, pyrazolidinyl, pyrrolinyl tetrahydropyranyl, tetrahydrothiopyranyl, piperidinyl, morpholinyl, dithianyl, thiomorpholinyl, piperazinyl, trithianyl, and diazepanyl; and wherein Z is $C_1$-$C_6$ alkyl or a bond.

2. The method of claim 1, wherein $R^{10}$ is selected from the group consisting of phenyl and tolyl, and $R^{11}$ is selected from the group consisting of phenyl, thienyl and chlorophenyl.

3. The method of claim 1, wherein $R^{12}$ is selected from the group consisting of allyl, 2-methylcyclohexyl, ethoxy, tetrahydrofuran-2-yl, tetrahydro-2H-thiopyran-4-yl, and Z is $C_1$-$C_3$ alkyl or a bond.

4. The method of claim 1, wherein an effective amount of a compound selected from the group consisting of N-allyl-3-phenyl-1-(p-tolyl)-1H-pyrazole-4-carboxamide, N-(2-methylcyclohexyl)-1-phenyl-3-(thiophen-2-yl)-1H-pyrazole-4-carboxamide, 3-(2-chlorophenyl)-N-(2-ethoxyethyl)-1-methyl-1H-pyrazole-4-carboxamide, 3-(2-chlorophenyl)-1-methyl-N-(2-(tetrahydrofuran-2-yl)ethyl)-1H-pyrazole-4-carboxamide, 3-(2-chlorophenyl)-1-methyl-N-(tetrahyrdo-2H-thiopyran-4-yl)-1H-pyrazole-4-carboxamide, and a salt thereof is administered to the plant, seed, soil or insect.

5. The method of claim 1, wherein the composition is administered to a seed.

6. The method of claim 1, wherein the composition is administered to a plant.

7. The method of claim 1, wherein the insect pest is selected from the group consisting of diamondback moth, fall armyworm, soybean looper, Western corn rootworm, Western tarnished plantbug and yellow fever mosquito.

8. The method of claim 2, wherein $R^{12}$ is selected from the group consisting of allyl, 2-methylcyclohexyl, ethoxy, tetrahydrofuran-2-yl, tetrahydro-2H-thiopyran-4-yl, and Z is $C_1$-$C_3$ alkyl or a bond.

9. The method of claim 8 wherein $R^{12}$ is an allyl.

10. The method of claim 1 wherein $R^{10}$ is selected from the group consisting of tolyl and methyl, and $R^{11}$ is selected from the group consisting of phenyl and chlorophenyl.

11. The method of claim 10 wherein $R^{12}$ is selected from the group consisting of allyl, 2-methylcyclohexyl, ethoxy, tetrahydrofuran-2-yl, tetrahydro-2H-thiopyran-4-yl, and Z is $C_1$-$C_3$ alkyl or a bond.

12. The method of claim 11 wherein $R^{12}$ is an allyl.

13. The method of claim 1, wherein $R^{10}$ is selected from the group consisting of p-tolyl, methyl, or phenyl; $R^{11}$ is selected from the group consisting of 2-chlorophenyl, 2-thienyl, or phenyl; $R^{12}$ is selected from the group consisting of allyl, 2-methylcyclohexyl, ethoxy, tetrahydrofuran-2-yl, tetrahydro-2H-thiopyran-4-yl, and Z is $C_1$-$C_3$ alkyl or a bond.

14. The method of claim 13 wherein the composition is administered to a seed.

15. The method of claim 13 wherein the composition is administered to a plant.

16. The method of claim 13 wherein the insect pest is selected from the group consisting of diamondback moth, fall armyworm, soybean looper, Western corn rootworm, Western tarnished plantbug and yellow fever mosquito.

\* \* \* \* \*